US006682754B2

(12) United States Patent
Emery et al.

(10) Patent No.: US 6,682,754 B2
(45) Date of Patent: *Jan. 27, 2004

(54) OVO DELIVERY OF AN IMMUNOGEN CONTAINING IMPLANT

(75) Inventors: Daryll A. Emery, New London, MN (US); Darren E. Straub, New London, MN (US)

(73) Assignee: Willmar Poultry Company, Inc., Willmar, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/449,271

(22) Filed: Nov. 24, 1999

(65) Prior Publication Data

US 2002/0034530 A1 Mar. 21, 2002

(51) Int. Cl.[7] .................... A61F 2/00; A61F 13/00; A61K 9/14; A61K 39/06
(52) U.S. Cl. ............... 424/426; 424/425; 424/423; 424/422; 424/489; 424/490; 424/484; 424/494; 424/184.1; 424/195.17; 106/501.1
(58) Field of Search ............. 424/195.17, 184.1, 424/484, 422, 494, 423, 425, 426, 489, 490; 119/6.8; 106/501.1

(56) References Cited

U.S. PATENT DOCUMENTS

| | | |
|---|---|---|
| 3,663,687 A | 5/1972 | Evans |
| 3,887,699 A | 6/1975 | Yolles ........................ 424/19 |
| 3,975,350 A | 8/1976 | Hudgin et al. ............. 260/30.4 |
| 4,164,560 A | 8/1979 | Folkman et al. ............... 424/22 |
| 4,180,560 A | 12/1979 | Katz et al. |
| 4,326,523 A | 4/1982 | Wolfrom et al. ............ 128/260 |
| 4,389,330 A | 6/1983 | Tice et al. .............. 427/213.36 |
| 4,452,775 A | 6/1984 | Kent ............................ 424/19 |
| 4,458,630 A | 7/1984 | Sharma et al. ................. 119/1 |
| 4,568,559 A | 2/1986 | Nuwayser et al. ............. 427/3 |
| 4,631,188 A | 12/1986 | Stoy et al. ..................... 424/81 |

(List continued on next page.)

FOREIGN PATENT DOCUMENTS

| | | |
|---|---|---|
| CA | 2029906 A1 | 9/1990 |
| EP | 287 206 A1 | 10/1988 |
| WO | WO 90/12591 A1 | 11/1990 |
| WO | WO 96/01620 | 1/1996 |
| WO | WO 97/13531 | 4/1997 |
| WO | WO 99/34667 | 7/1999 |
| WO | WO 99/43349 | 9/1999 |

OTHER PUBLICATIONS

Harlow, E. et al., "Antibodies: A Laboratory Manual", *Cold Spring Harbor Laboratory*, Chapter 5, pp. 72–87 (1988).

(List continued on next page.)

*Primary Examiner*—Christopher R. Tate
*Assistant Examiner*—Patricia Patten
(74) *Attorney, Agent, or Firm*—Mueting, Raasch & Gebhardt, P.A.

(57) ABSTRACT

The disclosure provides a method for administering an agent to an avian species by in ovo delivery of an implant releasably containing the agent. In one embodiment, the method is particularly advantageous for stimulating an immune response in a bird by in ovo administration of a biocompatible implant releasably containing an immunogen. The implant can provide for sustained or delayed release of the immunogen or both. The amount of immunogen that is released from the implant into the bird is preferably sufficient to effectively stimulate a primary immune response to the immunogen. Other agents which can be administered according to the method of the invention are disclosed.

14 Claims, 3 Drawing Sheets

U.S. PATENT DOCUMENTS

| | | | |
|---|---|---|---|
| 4,708,765 A | 11/1987 | Newman et al. | 156/626 |
| 4,709,765 A | 12/1987 | Campanell | 173/119 |
| 4,711,782 A | 12/1987 | Okada et al. | |
| 4,713,249 A | 12/1987 | Schröder | 424/488 |
| 4,756,907 A | 7/1988 | Beck et al. | 424/85 |
| 4,767,628 A | 8/1988 | Hutchinson | 424/426 |
| 4,863,735 A | 9/1989 | Kohn et al. | 424/422 |
| 4,897,268 A | 1/1990 | Tice et al. | 424/422 |
| 4,938,763 A | 7/1990 | Dunn et al. | 604/891.1 |
| 5,020,421 A | 6/1991 | Podlesak | 424/85.2 |
| 5,106,617 A | 4/1992 | Federicksen et al. | 424/422 |
| 5,114,719 A | 5/1992 | Sabel et al. | 424/422 |
| 5,153,002 A | 10/1992 | McMullen | |
| 5,158,038 A | 10/1992 | Sheeks et al. | 424/93 |
| 5,206,015 A | 4/1993 | Cox et al. | 424/93 |
| 5,219,554 A | 6/1993 | Groman et al. | |
| 5,232,984 A | 8/1993 | Hubbell et al. | 525/54.1 |
| 5,271,945 A | 12/1993 | Yoshioka et al. | |
| 5,311,841 A | 5/1994 | Thaxton | 604/51 |
| 5,324,519 A | 6/1994 | Dunn et al. | 424/426 |
| 5,339,766 A * | 8/1994 | Phelps et al. | 119/6.8 |
| 5,352,448 A | 10/1994 | Bowersock et al. | |
| 5,380,536 A | 1/1995 | Hubbell et al. | 424/497 |
| 5,397,568 A | 3/1995 | Whitfill et al. | 424/178.1 |
| 5,397,569 A | 3/1995 | Whitfill et al. | |
| 5,420,253 A | 5/1995 | Emery et al. | 530/423 |
| 5,427,791 A | 6/1995 | Ahmad et al. | 424/214.1 |
| 5,438,954 A | 8/1995 | Phelps et al. | 119/6.8 |
| 5,444,045 A | 8/1995 | Francis et al. | 514/12 |
| 5,534,256 A | 7/1996 | Potter et al. | |
| 5,538,733 A | 7/1996 | Emery et al. | 424/422 |
| 5,569,468 A | 10/1996 | Modi | 424/491 |
| 5,578,314 A | 11/1996 | Cochrum et al. | 424/424 |
| 5,641,745 A | 6/1997 | Ramtoola | 514/11 |
| 5,807,551 A * | 9/1998 | Reynolds | 424/159.1 |
| 5,830,479 A | 11/1998 | Emery et al. | 424/255.1 |
| 5,861,387 A * | 1/1999 | Labrie et al. | 514/169 |
| 5,902,565 A | 5/1999 | Cox et al. | |
| 5,906,826 A | 5/1999 | Emery et al. | 424/422 |
| 6,027,736 A | 2/2000 | Emery et al. | |

OTHER PUBLICATIONS

Kohn, J. et al., "Single–step immunization using a controlled release, biodegradable polymer with sustained adjuvant activity", *Journal of Immunological Methods*, vol. 95, pp. 31–38 (1986).

Male, D. et al., "Advanced Immunology", *J.B. Lippincott Company*, Chapter 14, pp. 14.1–14.10 (1987).

Malkinson, M., "The Transmission of Passive Immunity to *Escherichia coli* from Mother to Young in the Domestic Fowl (*Gallus domesticus*)", *Immunology*, vol. 9, pp. 311–317 (1965).

Merrifield, R.B., "Solid Phase Peptide Synthesis. I. The Synthesis of a Tetrapeptide", *Journal of the American Chemical Society*, vol. 85, No. 14, pp. 2149–2154 (Jul. 20, 1963).

Merrifield, R.B., "Automated Synthesis of Peptides", *Science*, vol. 150, No. 3693, pp. 178–185 (Oct. 8, 1965).

Merrifield, B., "Solid Phase Synthesis", *Science*, vol. 232, pp. 341–347, (Apr. 18, 1986).

Niemi, S. et al., "Evaluation of Ethylene—Vinyl Acetate Copolymer as a Non–Inflammatory Alternative to Freund's Complete Adjuvant in Rabbits", *Laboratory Animal Science*, vol. 35, No. 6, pp. 609–612 (Dec. 1985).

Patterson, R. et al., "Antibody Production and Transfer to Egg Yolk in Chickens", *The Journal of Immunology*, vol. 89, pp. 272–278 (1962).

Rose, M. et al., "Immunoglobulins in the Egg, Embryo and Young Chick", *Development and Comparative Immunology*, vol. 5, No. 1, pp. 15–20 (1981).

Radomsky, M. et al., "Controlled Vaginal Delivery of Antibodies in the Mouse", *Biology of Reproduction*, vol. 47, No. 1, pp. 133–140 (Jul. 1992).

Ulmer, J. et al., "Heterologous Protection Against Influenza by Injection of DNA Encoding a Viral Protein", *Science*, vol. 259, No. 5102, pp. 1745–1749 (Mar. 19, 1993).

Bolin, C. A. et al., "Passive immunization with antibodies against iron–regulated outer membrane proteins protects turkeys from *Escherichia coli* septicemia," *Infect Immun.* May 1987;55(5):1239–42.

Bouchet, A. et al., "Immunological variants of the aerobactin–cloacin DF13 outer membrane protein receptor IutA among enteric bacteria," *Infect Immun.* Jul. 1994;62(7):3017–21.

Bragg, P. D. et al., "Organization of proteins in the native and reformed outer membrane of *Escherichia coli*,"*Biochim Biophys Acta.* Aug. 9, 1972;274(2):478–88.

Chart, H. et al., "Antigenic and molecular homology of the ferric enterobactin receptor protein of *Escherichia coli*," *J Gen Microbiol.* Jun. 1985;131(Pt 6): 1503–9.

Choi–Kim, K. et al., "Relationship between the iron regulated outer membrane proteins and the outer membrane proteins of in vivo grown *Pasteurella multocida*," *Vet Microbiol.* Jun. 1991;28(1):75–92.

Cleland, J. L., "Single–administration vaccines: controlled–release technology to mimic repeated immunizations," *Trends Biotechnol.*Jan. 1999;17(1):25–29.

Glisson, J. R. et al., "Cross–protection studies with *Pasteurella multocida* bacterins prepared from bacteria propagated in iron–depleted medium," *Avian Dis.* Oct.–Dec. 1993;37(4):1074–9.

Griffiths, E. et al., "Pathogenic *Escherichia coli*express new outer membrane proteins with growing in vivo," *FEMS Microbiol Lett.* 1983;16:95–99.

Hancock, R. E. W. et al., "Iron transport of *Escherichia coli* K–12: involvement of the colicin B receptor and of a citrate–inducible protein," *J Bacteriol.* Sep. 1976;127(3):1370–5.

Hudson, L. et al., "Lymphokines and Cytokines," *Practical Immunology, 3rd Ed..*, Blackwell Scientific Publications, London, England (1989) pp. 423–441.

Ikeda, J. S. et al., "Antigenically related iron–regulated outer membrane proteins produced by different somatic serotypes of *Pasteurella multocida*," *Infect Immun.* Sep. 1988;56(9):2499–502.

Ogunnariwo, J. A. et al., "Evidence for non–siderophore–mediated acquisition of transferrin–bound iron by *Pasteurella multocida*," *Microb Pathog.* Jul. 1991;11(1):47–56.

Rimler, R. B., "Cross–protection factor(s) of *Pasteurella multocida*: passive immunization of turkeys against fowl cholera caused by different serotypes," *Avian Dis.* Oct.–Dec. 1987;31(4):884–7.

Rimler, R. B. et al., "Solubilization of membrane–associated cross–protection factor(s) of *Pasteurella multocida*," *Avian Dis.* Apr.–Jun. 1989;33(2):258–63.

Rimler, R. B., "Partial purification of cross–protection factor(s) from *Pasteurella multocida*," *Avian Dis.* Oct.–Dec. 1994;38(4):778–89.

Roitt, I. M. et al., "16—Immunity to Viruses, Bacteria and Fungi," and "17—Immunity to Protozoa and Worms," *Immunology, 2ⁿᵈ Ed.*, C.V. Mosby Company, St. Louis, MO (1989) pp. 16.1–17.21.

Snipes K. P., "Plasma– and iron–regulated expression of high molecular weight outer membrane proteins by *Pasteurella multocida*," *Am J Vet Res.* Aug. 1988; 49(8):1336–8.

Williams, P. et al., "Novel aerobactin receptor in *Klebsiella pneumoniae*," *J Gen Microbiol.* Dec. 1989;135(PT 12):3173–81.

Yearout, D. R., "Prevention and treatment of aspergillosis by vaccination: a new protocol," *Proceedings of the 1988 Annual Meeting of the Association of Avian Veterinarians*, Association of Avian Veterinarians, Boca Raton, FL (1988), pp. 139–144.

Zhao, G. et al., "Expression of iron–regulated outer membrane proteins by porcine strains of *Pasteurella multocida*," *Can J Vet Res.* Jan. 1995;59(1):46–50.

Banerjee–Bhatnagar et al., "Expression of *Neisseria meningitidis* Iron–regulated outer membrane proteins, including a 70–kilodalton transferrin receptor, and their potential for use as vaccines," *Infect Immun.* Sep. 1990; 58(9):2875–81.

Brogden et al., "Lysates of turkey–grown *Pasteurella multocida*: effects of solubilizing agents on the immunologic properties of membrane vesicles," *Am J Vet Res.* Mar. 1983; 44(3):428–32.

Crichton, "Inorganic Biochemistry of Iron Metabolism," Chapter 3: Microbial iron uptake and intracellular release, Ellis Horwood, pp. 59–76 (1991).

Danve et al., "Transferrin–binding proteins isolated from *Neisseria meningitidis* elicit protective and bactericidal antibodies in laboratory animals," *Vaccine.* Sep. 1993; 11(12):1214–20.

Erdei et al., "Lactoferrin binds to porins OmpF and OmpC in *Escherichia coli*", *Infection and Immunity*, Apr. 1994; 62(4):1236–1240.

Gilleland, Jr. et al., "Perspectives on the potential for successful development of outer membrane protein vaccines," *Eur J Clin Microbiol.* Jun 1987;6(3):231–3. Review. (No abstract available.).

Lu et al., "The outer membrane of *Pasteurella multocida* 3:A protects rabbits against homologous challenge," *Infect Immun.* Dec. 1991;59(12):4517–23.

Male et al., "Advanced Immunology," Chapter 11, pp. 11.1–11.16., J.B. Lippincott Company, Philadelphia, PA (1991).

Stuart et al., "Iron–suppressible production of hydroxamate by *Escherichia coli* isolates," *Infect Immun.* Jun. 1982;36(3):870–5.

Truscott et al., "Demonstration of an outer membrane protein with antiphagocytic activity from *Pasteurella multocida* of avian origin," *Infect Immun.* Jun. 1988; 56(6):1538–44.

Visca et al., "Siderophore production by *Salmonella species* isolated from different sources," *FEMS Microbiol Lett.* Apr. 15, 1991;63(2–3);225–31.

* cited by examiner

OVO DELIVERY OF AN IMMUNOGEN CONTAINING IMPLANT

BACKGROUND OF THE INVENTION

In the first few weeks of life a newborn chick, poult, duckling or other avian hatchling ("chick") is relatively incompetent at producing antibodies in response to antigenic stimuli. During this period, a significant amount of resistance to infectious diseases is provided by passive immunity derived from maternal antibodies of the hen. However, the presence of passive immunity can also contribute to the immuno-incompetence of the chick during the early post hatching period.

Passive immunity is transferred from the hen to the chick via the egg. IgY antibodies are sequestered from the hen's serum and secreted in the ovary and incorporated in the yolk before ovulation. The antibodies are stored in the yolk until the later stages of embryonic development when they are absorbed by the embryonic membranes and transferred to the circulation of the chick to provide passive immunity.

Maternally derived antibodies provide immunological protection of the developing chick before active antibody production occurs. However, the presence of maternal antibodies can also interfere with the ability of the young bird to actively respond to an immunogen through a mechanism involving antigen elimination which prevents active immunity to that antigen. Thus, maternal antibodies can act to regulate the immune response by inhibiting development of antibody producing cells.

Typically, food producing animals such as poultry and other livestock (e.g., cattle, swine, sheep, fish, etc.) are immunized as a group at a set period of time. However, within a given population of animals, there are generally variations in the level of maternal antibody and maturation of the immune system between individual animals. For example, chicks from a commercial hatchery may come from many different breeding farms, each having different types and different levels of passive antibodies. In fact, chicks from the same breeder flock may have highly variable antibody titers to the same disease agent. This non-uniformity of passive immune protection can significantly influence the effectiveness of a vaccination program.

In the poultry industry, conventional vaccination programs are designed to be administered after the decline of maternal antibody, typically starting at about 3–4 weeks of age. Under commercial rearing conditions of poultry it is often not feasible to use an injectable vaccine or to immunize birds on an individual basis due to the large number of birds within a flock. Generally, a modified live vaccine is administered by aerosol or water administration at a time at which there is an estimated decline in the level of circulating maternal antibodies against the antigen. However, using live vaccines in the presence of maternal antibodies has a number of inherent disadvantages. For example, to provide sufficient immune stimulation, a live vaccine generally must replicate in the host. The presence of maternal antibodies to that antigen can inhibit replication of a live immunogen resulting in insufficient levels of the immunogen to stimulate an immune response, resulting in a failure to stimulate active immunity. In addition, the consumption of maternal antibodies which were used to inhibit replication of the live immunogen can leave the animal without passive protection. Together or individually, these events can leave the bird unprotected against a field challenge.

Live vaccines also cause significant reactions which can result in decreased body weight, increased mortality, increased medication costs and increased condemnations. The generally held view in the industry's use of modified live vaccines is that vaccine reaction is a normal and accepted fact of live respiratory vaccine administration and is indicative of the response by the body's immune system. However, adverse vaccine reactions do not serve a useful purpose and preferably should be prevented.

To overcome the potential problems of vaccinating in the presence of neutralizing maternal antibodies, vaccination programs are used which require administration of multiple immunizations. According to some programs, birds are immunized by aerosol application at, for example, one day, 10–14 days and 21 days of age. The first vaccination is to present the vaccine to those birds that have little or no circulating maternal antibodies. In these birds, the vaccine will induce an immune response and induce a level of protection to prevent early mortality as well as prevent amplifiers of the field virus which could expose the remaining flock to a potential disease outbreak. Subsequent vaccination at days 10–14 and day 21 are to immunize those individuals not responsive to prior immunization due to presence of maternal antibodies.

Another approach to overcome potential problems of vaccinating in the presence of maternal antibodies is to vaccinate an animal with an immunogen repeatedly from day one until they are capable of responding. The stress on the animal and expense for the breeder makes this an unfeasible alternative. In fact, one problem with any repeated immunization program is the requirement for increased handling of the animals which causes stress that can result in a significant reduction in weight gain and efficient feed conversion.

Young animals, including birds can also be immunized en masse after all animals have lost maternal antibodies. A drawback, however, is that there will be a certain percentage of animals who lose passive protection before others and are therefore vulnerable to infection before they are vaccinated.

Yet another approach is to administer, to a young animal, a primary immunizing dose of an immunogen in a preparation that will present the immunogen in a slowly dissipating material. Such preparations include, for example, an injectable water-in-oil emulsion containing a killed antigen, a suspension of an antigen in Freund's complete adjuvant or phosphatidylcholine (egg-lecithin)- or cholesterol-based liposomes containing an entrapped immunogen. However, such preparations do not provide adequate long-term delivery of an immunogen and may cause adverse reactions such as a granuloma at the site of injection. In addition, there is a risk that the person administering the injection accidentally injects themselves with the preparation, resulting in an adverse reaction from the injected ingredients.

A method for administering a biocompatible implant containing an immunogen at 1–90 days after hatching is disclosed in U.S. Pat. No. 5,538,733, the entire disclosure of this patent is incorporated herein. Methods for in ovo immunization of an avian by injecting a liquid immunogen preparation into a fertile egg during incubation are also known. Such methods of immunization, however, are still subject to the interfering affects of circulating maternal antibodies. That is, interfering maternal antibodies against bacteria, viruses or other agents to which the hen has been exposed are present in the yolk albumin, anmiotic and allantoic fluids and serum throughout embryonic development, prior to hatching. For example, it has been shown that the immunoglobulin IgG is present in the yolk throughout incubation and becomes distributed to the albumen at four days of embryogenesis and in the amniotic as well as in the allantoic fluid at about 12–14 days of incubation. Rose et al., *Development and Comparative Immunology*, 5:15–20 (1981). IgG is present in the embryo serum from about the 12$^{th}$ day of incubation and in small amounts in the intestine on about the 19$^{th}$ day. Immunoglobulins IgM and IgA have not been shown to be present in the yolk but are present in the albumen and amniotic fluids during about the 12$^{th}$ and 17$^{th}$ day of embryogenesis. Thus, the presence of these maternal antibodies still affect a young bird's response to a vaccine antigen even if administered in ovo.

Accordingly, there is a need for a method of administering an immunogen to a young bird that can circumvent the interfering affects of maternal antibodies while providing a stimulus for active immunity at the point when the bird is capable of responding to the immunogen. There is also a need to reduce the handling of birds and number of repeat administrations of an immunogen which are presently necessary to assure stimulation of active immunity in substantially all birds of a population.

SUMMARY OF THE INVENTION

It will be appreciated that throughout the specification guidance may be provided through lists of examples. In each instance, the recited list serves only as a representative group. It is not meant, however, that the lists are exclusive.

The present disclosure is directed to implants and methods for delivering an agent to an animal. The invention can be particularly advantageous for delivering an agent to a bird in ovo. In one embodiment, the agent can be an immunogen and the method used to induce active immunity in a young bird. This embodiment provides for stimulating active immunity in a population of birds regardless of the immune status of an individual bird. The embodiment advantageously reduces handling, administration repetition and costs associated with most presently available immunization systems.

According to a preferred embodiment of the invention, an immunogen is contained within an implant, or multiple implants, that are administered to a bird in ovo and released into the tissues after administration. In preferred embodiments, the immunogen can be released from the implant at a predetermined time. Thus, a single administration of an immunogen to a population of birds can provide stimulation of active immunity in an individual bird when the individual is sufficiently immunocompetent to mount an immune response against that immunogen.

An implant of the invention can provide for delayed release, sustained release, or a combination thereof, of the immunogen at a selected time after administration. In ovo administration of an immunogen contained in an implant has numerous advantages over conventional vaccination techniques. For example, in ovo administration can reduce the stress associated with handling of the bird. In addition, sustained or delayed release of an immunogen enables each individual bird in a flock to respond to the antigen when the bird becomes immunocompetent. Thus, the internal variability of response to immunization in a flock is reduced and overall vaccine efficacy is increased. The method also reduces vaccine reactions that are often associated with administration of modified live vaccines.

DETAILED DESCRIPTION

Figure 1:
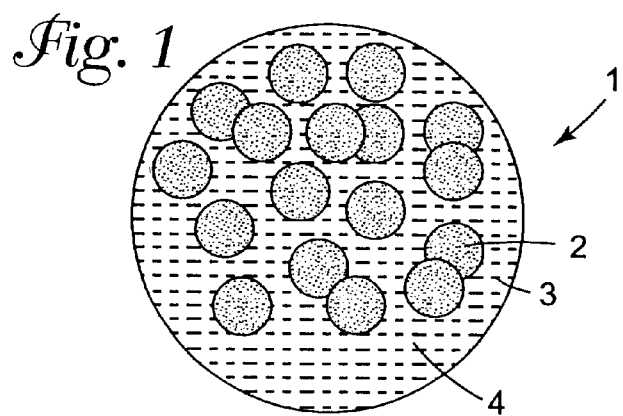
FIG. 1 is a diagrammatic illustration of one embodiment of a timed release implant according to the invention.

As used herein, the term "bird" includes turkeys, chickens, ducks, geese, pheasants, ostriches and other avian species.

The terms "immunogen" and "antigen" are used synonymously throughout the disclosure and mean a substance or entity that is structurally or functionally capable of inducing an immune response in a bird. This includes, but is not limited to, inactivated whole microorganisms, attenuated whole microorganisms, whole viral particles, antigenic microorganism/viral components or fragments, chemically or physically modified antigens, recombinant antigens, and other antigens or combinations thereof.

As used herein, the terms "immunocompetent" and "immunologically competent" refer to a state when a bird is capable of mounting an active immune response to a particular immunogen. Immune system immaturity or immuno-incompetency can result in the inability of a bird to actively respond to a particular immunogen. The, presence of circulating maternal antibodies against a particular immunogen can be a part of immuno-incompetency and can inhibit the ability to mount an active immune response by preventing exposure of the immunogen to the chick's immune system. Other factors can also play a role in the ability of a young bird to mount an active immune response against an immunogen.

The invention addresses the difficulty of consistently inducing an active immune response to an immunogen in a flock of birds who have varying levels of neutralizing maternal antibodies and differences in the state of maturation of the immune system. According to the invention, administration of an immunogen containing implant which is capable of sustained and/or delayed release of the immunogen provides for presentation of the immunogen to an individual bird at the "critical point." The "critical point" is the point in time when the bird is capable of mounting an active immune response to a particular antigen.

In general, the method of the invention includes administering an implant containing a "releasable agent" such as an immunogen to a bird in ovo. In addition to an antigen, the "releasable agent" can comprise, for example, an antibody, immune regulating agent, antibacterial agent, antiviral agent, antifungal agent, anticoccidial agent, etc. If the releasable agent is an antibody it may be an antibody specific for a particular disease agent or non-specific, for example, to help enhance resistance to a disease or to extend the level of circulating maternal antibody.

Depending on the particular implant selected, the release of the agent can occur before or after hatching. The implant may provide a sustained or delayed release of the agent at a predetermined time after administration. When the agent is an immunogen, the invention can provide for a single in ovo administration of a large number of eggs while providing the effect of immunizing each hatchling at its individual critical point.

By exposing the hatchling's immune system to a particular antigen at the critical point, the "vulnerability period" to that antigen is reduced. The "vulnerability period" is the period after passive immunity has waned but before protective levels of active immunity has commenced. By reducing the vulnerability period the method can advantageously reduce the incidence of infection or mortality in young birds.

In one embodiment, the in ovo administration of an immunogen, such as one or more siderophore receptor proteins (SRP), can advantageously facilitate growth performance in birds receiving the immunogen.

As used herein, in ovo injection of an implant can result in placement of the implant into the flesh of the embryonating chick, yolk sac, amnion, albumin or allantoic fluids, surrounding the egg or in the air cell.

In ovo injection techniques for liquid vaccines, vitamins, nutrients and other compositions, are known. See e.g., U.S. Pat. No. 4,458,630 to Sharma, et al.; U.S. Pat. No. 5,158,038 to Sheeks, et al.; and U.S. Pat. Nos. 5,339,766 and 5,438,954 issued to Phelps, et al. These methods of injection may be utilized according to the present invention. Generally, the implant is injected into the blunt end of the egg, preferably during the last quarter of incubation. A convenient time for in ovo immunization in a commercial hatchery is during transfer. Transfer is the time when eggs are removed from the incubator and placed into a hatcher, typically at about 17–19 days for chickens and 25–27 days for turkeys.

A preferred implant according to the invention is biocompatible. The implant can provide sustained or delayed release of the immunogen or a combination thereof. Various implant matrix formulations are known and can be used depending on the desired time, rate and duration of immunogen release. Breeder immune status, farm history, environmental conditions, serum studies, incubation parameter, and other factors may be considered in determining the release characteristics of a particular implant for a particular application.

If a sustained release implant is used, the immunogen can be released for up to 90 days, preferably about 30–90 days after administration of the implant. Release of immunogen from a sustained release implant can begin at about 1 to 60 days, typically about 1 to 21 days after administration. If a delayed release implant is used, the immunogen can be released from the implant at 1 to 60 days, typically about 7–21 days after administration.

The amount of immunogen that is released from the implant into the bird preferably stimulates a primary immune response in a bird. As used herein, a "primary immune response" means that the immunization provides sufficient antigen recognition by the bird to cause an anamnestic (secondary) immune response upon subsequent exposure to the immunogen by natural exposure or booster immunization. The booster immunization can be provided by known methods. Alternatively, a booster immunization can be provided by in ovo immunization with a single implant providing sustained release of the immunogen, a single implant providing two or more different release characteristics (e.g., sustained release and delayed release) or administering two or more implants each having a different release characteristic.

I. Implant

Implants according to the invention include known implant matrices suitable for administration in living tissues. Typically, the implant matrix comprises a biocompatible, non-toxic material that allows for incorporation of an immunogen and release of the immunogen into the bird at a desired time after hatching. The implant may or may not be biodegradable, bioerodible or bioabsorbable.

As used herein, the term "biocompatible" means that the implant matrix does not cause substantial tissue irritation or necrosis at the implant site. The term "biodegradable" means that the implant matrix degrades over time by enzymatic or hydrolytic action, or other mechanism in the animal's body. The term "bioerodible," means that the implant erodes or degrades over time by contact with surrounding tissue fluids, through cellular activity or other physiological degradation mechanisms. By "bioabsorbable," it is meant that the implant matrix breaks down and is absorbed by a cell, tissue, or other mechanism within the animal's body.

The immunogen can be released from the implant as a sustained release, delayed release or a combination thereof. Preferably, the amount of immunogen that is released is effective to induce a primary immune response to the immunogen.

A preferred implant can be made from a biocompatible solid phase polymeric matrix that allows for structural integrity and is bioabsorbable, biodegradable, and/or bioerodible in the body of the bird and will not cause irritation or an adverse effect in the body of the bird. The implant can be administered as a single unit or multiples thereof, each may have the same release kinetics or a combination of different release times A sustained release implant provides release of an immunogen in a substantially continuous manner. Sustained release of an immunogen from an implant can begin at about 1–48 hours after administration, typically about 24 hours depending on the composition of the implant matrix. Various known coatings, including polymer coatings, can also be applied to the implant to affect the time at which the sustained release of the immunogen begins. Examples of suitable sustained release implant matrices include polymeric matrix delivery systems such as disclosed in U.S. Pat. No. 4,164,560 and cholesterol matrix delivery systems such as disclosed in U.S. Pat. No. 4,452,775. Other matrices include cellulosic polymers, copolymers of D-mannuronic acid and L-guluronic acid, polylactide, polycaprolactone, polyglycolides, etc.

A delayed release implant matrix can provide a "pulse" or "burst" of immunogen release from the implant at a predetermined time post hatching. Different matrices provide immunogen release at different times. Typically, a delayed release implant matrix will be selected to provide immunogen release at, or after, the estimated critical point for a particular group of hatchlings. Flock history, serum analysis, or other appropriate method for measuring passive antibody levels can be used to determine suitable time of release for a particular flock of a particular immunogen for a particular flock. Suitable delayed release implant matrices are discussed below.

It is foreseen, however, that some parameter other than the herein defined "critical point" may be used as the determinate for selection of the release characteristics of a particular implant system selected for a particular application.

In one embodiment a combination of a sustained release and a delayed release matrix can be used. Such implants could provide for early release of an immunogen to stimulate an immune response in those birds with low initial levels of maternal antibody, followed by a burst of antigen at a later time, when levels of maternal antibody in most of the flock has sufficiently declined for maximizing the efficacy of the immunization.

An implant matrix can include a core containing the immunogen or other releasable agent and an outer coating. Both the core and coating compositions can affect timing and rate of immunogen release.

Generally, the core can include excipients, lactose, fibrin, methylcellulose, collagen, cholesterol, carbowax, dibutylphthalate (DBP) polyvinyl pyrrolidene (PVP), zinc or magnesium stearate, stearic acid, polyethylene glycol (PEG), silica, etc. Examples of preferred excipient materials include D, L-lactide, polyacetal polymers, polyorthoesters, polyesteramides, polycaprolactone, polycarbonates, polyhydroxy buterate, polymaleamides, etc.

Typically, the outer coating can be a polymer. Examples of useful polymers for forming an outer coating that is biodegradable and bioabsorbable include polycationic polymers, including, for example, polylysine, polyornithine, polyethyleneimine and polylactides, polyglycolides, polycaprolactones, polyanhydrides, polyamides, or copolymers thereof such as copolymers of polyamides and polyesters, copolymers of PLA and PGA, etc. In general, the in vivo life of an implant formulated with such polymers will depend at least in part, on the molecular weight and degree of crosslinking of the polymer in the matrix. Formulations for such matrices are known in the art, as disclosed for example, in U.S. Pat. No. 3,887,699 to Yolles and U.S. Pat. No. B1 4,767,628 to Hutchinson (ICI). Another useful biodegradable implant material for a syringeable, in-situ forming solid implant made of a thermoplastic or thermosetting polymer system is described in U.S. Pat. Nos. 4,938,763 and 5,324,519 to Dunn et al.

The implant can be formulated to provide delayed and sustained release of an immunogen. According to one embodiment, timing and rate of release can be a result of the excipient used. Each excipient providing a particle which releases immunogen at a different rate. Hence, a single implant providing sustained and delayed release can include a mixture of particles having different release rates which are administered as a single injection. By varying the excipient, the immunogen can provide sustained release for an initial period of time by the first biodegradable particle. A second set of particles, providing delayed release can then begin to release as the first particle delivery begins to decline. This could be followed by a third and fourth set of particles within the same injection each having different rates of release.

Other implants useful in the method include biodegradable, metabolizable, cholesterol-based pellets that provide for slow release of bioactive substances. Cholesterol-based implant matrices are commercially-available, for example, as 21, 60, and 90-day implants from Innovative Research, Saratoga, Fla. Other cholesterol-based implants have been described for slow release of biotin and other micronutrients, and proteins, polynucleotides, polysaccharides, for example, U.S. Pat. No. 4,452,775 to Kent; and U.S. Pat. No. 4,326,523 to Wolfrom. Also useful are implants having a peptide/polymer matrix, for example, tyrosine dipeptides and polymers as described in U.S. Pat. No. 4,863,735 to Kohn, and Kohn et al., *J. Immunol. Methods* 95:31–38 (1986), that will degrade to form a product having adjuvant activity for the antigen or other bioactive compound incorporated into the matrix.

Although not preferred for certain indications, an implant made of a non-erodible, non-biodegradable synthetic polymer, as for example, a hydrogel, a high density polyethylene, or ethylene-vinyl acetate copolymer (EVAC), may be used according to the method for sustained delivery of the immunogen. Such implant matrices are described, for example, by Niemi et al., *Laboratory Animal Science* 35:609 (1985) (EVAC); Radomsky et al., *Biol. Reprod.* 47:133–140 (1992) (EVAC); U.S. Pat. No. 5,114,719 to Sabel (EVAC et al.); and U.S. Pat. No. 3,975,350 to Hudgin (hydrogel carrier). However, such implants do not naturally degrade in the body and require surgical removal after the immunogen has been delivered into the body of the animal. In addition, EVAC implants have been shown to cause irritation resulting in necrosis at the implant site. Hydrogels are a polymeric material that swell but will not dissolve in water, and have a structural rigidity imparted by crosslinking agents, as for example, polyhydroxyalkyl methacrylates (P-HEMA), polyacrylamide, polymethacrylamide, polyvinyl pyrollidone, polyvinyl alcohol (PVA), among others. Low molecular weight substances tend to diffuse relatively quickly through a hydrogel matrix which may be a disadvantage for controlled delivery. Another material is an injectable, nonbiodegradable, polymeric composition that solidifies when placed in contact with tissue fluids by absorption of water as described in U.S. Pat. No. 4,631,188 to Stoy.

The matrix may optionally be formulated to include a soluble or insoluble core-forming agent that will dissipate from the matrix into surrounding tissue fluids causing the formation of pores and/or channels throughout the implant matrix. Examples of such pore-forming agents include sodium chloride, calcium carbonate, calcium phosphate and other salts; carboxymethylcellulose, polyethylene glycol, sodium alginate, agarose and other polymers; starch, glucose and other carbohydrates; amino acids and low molecular weight non-immunogenic proteins etc.

II. Agents

Various agents or "payload" can be released from an implant of the invention. Such agents include, for example, immunogens, adjuvants, antibodies, nutrients, antibiotics, anti-viral agents, antifungal agents, anticoccidial agents, etc.

A. Immunogen.

According to the invention, an immunogen has a chemical structure which provides for incorporation of the immunogen into the implant matrix such that the immunogen will be released from the matrix, preferably at a predetermined time. The immunogen may be any antigenic substance that is capable of stimulating an immune response in the bird being immunized.

The implant may be formulated to include a single immunogen or a mixture of immunogens for immunizing the bird against one or more antigenic agents. The immunogen may also be formulated in multiple implants with different release kinetics but given as a single administration.

The immunogen may be derived from pathogenic or non-pathogenic organisms such as a bacteria, virus, fungi, mold, protozoans, nematodes, etc. The immunogen may be in the form of, for example, whole bacterial cells, whole viral particles, plasmids, naked DNA or RNA, immunogenic subunit molecules or secreted substances derive therefrom, isolated nucleic acid, preferably bound to a carrier protein, etc. Immunogens may be prepared according to conventional isolation and purification methods, and/or by gene expression according to recombinant DNA techniques to make and express a gene encoding all or part of an antigenic peptide chain in an appropriate vector (i.e., vaccinia and/or herpes virus recombinants). Such immunogenic subunits include, for example, subunit vaccine polypeptides, cell membrane glycoproteins, polysaccharides, sphingolipids, lipopolysaccharides, etc. See, for example, Harlow and Lane, *Antibodies, A Laboratory Manual*, generally and Chapter 5, Cold Spring Harbor Laboratory, Cold Spring Harbor, New York, N.Y. (1988); Male et al., Advanced Immunology, generally an pages 14.1–14.15, J.B. Lippincott Co., Philadelphia, Pa. (1991); and Roitt et al., *Immunology*, generally and pages 16.1–17.21, C.V. Mosby Company, St. Louis, MO (1989).

Also useful are immunogenic synthetic peptides that mimic antigenic peptide sequences. Such immunogens may be synthesized using a solid-phase technique as described, for example, in R. B. Merrifield, *Science* 85: 2149–2154 (1963), purified, and optionally coupled to a carrier protein such as muramyldipeptide (MDP), bovine serum albumin (BSA), keyhole limpet hemocyanin (KLH), or other carrier proteins, using a bifunctional coupling agent such as glutaraldehyde, or other suitable agent.

Other immunogens include purified, secreted antigen virulence factors, such as toxins or cytotoxins. Toxin antigens which are detoxified by modifying (toxoids), preferably administered in combination with an adjuvant such as aluminum hydroxide, may be used to stimulate the formation of toxin-neutralizing antibodies. Examples of toxins that may be used as an immunogen include bacterial endotoxins, exotoxins and enterotoxins Also useful is a hapten, or low molecular weight substance such as an antibiotic, drug, peptide, among others, which when conjugated to an immunogenic carrier such as a protein, carbohydrate, lipid, or other like carrier, for example, BSA and KLH, using a bifunctional coupling agent, will induce an immune response directed against the parts of the conjugate. The preparation of hapten immunogens is described, for example, in Harlow and Lane, *Antibodies: A Laboratory Manual*, pages 72–87, Cold Spring Harbor Laboratory, Cold Spring Harbor, New York, N.Y. (1988).

Another immunogen is an anti-idiotype antibody that reacts with the antigen binding site of the idiotype antibody, and structurally mimics the epitope, i.e., contains the internal image of the epitope. The anti-idiotype may be used as an immunogen to induce antibodies against the original epitope. Briefly, anti-idiotypic antibodies may be induced by injecting an antigen into a rabbit and allowing the immune system to produce immunoglobulins. These immunoglobulins are then harvested and injected into a second animal such as a domestic hen. The hen then mounts an immune response to the foreign antibodies with the production of immunoglobulins that mimic the original antigen. Anti-idiotype antibodies may then be isolated from the yolks of eggs laid by the hen by methods known in the art, and used as an original immunogen. A useful method for isolating antibodies from egg yolks is according to the method described in U.S. Pat. No. 5,420,253, entitled "Method for Purifying Egg Yolk Immunoglobulins."

The immunogen may also be derived from RNA or DNA viruses. Examples of such viruses include New Castle disease virus (NCV), hemorrhagic enteriditis virus (HEV), infectious rhinotracheitis virus (IBRV), fowl pox virus, avian leukosis virus, infectious bursal disease virus, infectious bronchitis virus, avian influenza virus, avian encephalomyelitis virus, iridoviridae, herpeviridae, rhabdoviridae, birnavirdae, among others. Techniques for the preparation of virus-derived immunogens are known in the art, and described, for example, in Ulmer et al., *Science* 259: 1745 (1993); Male et al., *Advanced Immunology, pages 14.1–14.15*, J. B. Lippincott Co., Philadelphia, Pa. (1989).

Immunogens may also be derived from gram-negative bacteria such as *Escherichia coli;* Salmonella spp. such as *Salmonella agona, Salmonella blockley, Salmonella enteriditis, Salmonella typhimurium, Salmonella hadar, Salmonella heidelberg, Salmonella montevideo, Salmonella senftenberg, Salmonella cholerasuis;* Pasteurella spp. such as *Pasteurella haemolytica* and *Pasteurella multocida;* Pseudomonas spp. such as *Pseudomonas aeruginosa;* Klebsiella spp. such as *Klebsiella pneumoniae;* Actinobacillus spp.; Haemophilus spp.; *Ornithobacterium rhinotracheale* (ORT); Bordetella spp. such as *B. avium;* Myxcobacteria spp.; Sporocytophaga spp.; Chondrococcus spp.; Cytophaga spp.; Flexibacter spp.; Flavobacterium spp.; Aeromonas spp.; Yersinia spp.; Vibrio spp.; among other gram-negative bacteria. Examples of gram positive bacteria from which useful immunogens may be derived include Staphylococcus spp., Streptococcus spp., Erysipelothrix spp., Clostridium spp., *Renibacterium salmoninarum;* among others.

The immunogen may also be derived from a fungi or mold such as *Aspergillus flavus; Aspergillus fumigatis;* Penicillium spp.; Fusarium spp.; Candida spp. such as *C. albicans;* Trichophyton spp.; Rhizopus spp.; Nocardia spp.; Branchiomyers spp.; Exophiala spp.; and other fungi and molds; protozoa such as Cryptococcus, Coccidia, Giardia, among others; spirochetes such as Borrelia spp.; nematodes including Ascaris spp., Trichinella spp., and the like, helminthes such as flukes, tapeworms, among others; and other like pathogenic organisms. Methods for preparing immunogens derived from fungi, molds, protozoa, nematodes, and helminthes are known in the art, and described, for example, by Douglas R. Yearout, 1988 *Proc. Assoc. of Avian Veterinarians,* pages 139–144 (1988) (aspergillus).

Other useful immunogenic agents include conserved siderophore receptor proteins (SRP) and porins which are a protein or subunit immunogenic peptide of a protein derived from the outer membrane of a gram-negative and gram-positive bacteria or other pathogenic organism such as a mold or fungus, that will bind a siderophore, or iron-binding protein. Implants containing an SRP immunogen can be administered to elicit an immune response in a bird with the production of anti-SRP antibodies that react with SRPs of the same organism from which the SRP immunogen was derived or cross-react with a SRP of a pathogenic organism of a different strain, species or genus. Examples of siderophore receptor proteins are hydroxamates and phenolates such as aerobactin, enterochelin, citrate, ferrichrome, coprogen, etc., or an immunogenic fragment thereof, that will stimulate production of anti-SRP antibodies. The transmembrane and/or porin proteins which are highly conserved among gram-negative bacteria particularly belonging to the Enterobacteriaceae family can be combined with the SRPs to produce a highly conserved vaccine composition that cross-reacts with multiple strains, species and genera of gram-negative bacteria. Examples of suitable SRP immunogens are disclosed in U.S. Pat. No. 5,830,479, the entire disclosure of which is incorporated herein by reference.

As stated earlier, in addition to antigens, the releasable agent or payload of the implant can also be a protein such as an antibody. Thus, according to this aspect of the invention, the implant could provide a sustained or delayed release of antibodies selected against a particular agent such as New Castle disease virus (NDV) or hemorrhagic enteriditis virus (HEV). These antibodies can provide passive protection at a selected period of time. Thus, by selecting a particular sustained or delayed release matrix, antibodies can be released at a selected period of time when it is believed that such passive protection may be most beneficial to the bird. See e.g., U.S. Pat. No. 5,420,253.

B. Adjuvants and Immunomodulators.

An implant may also include physiologically-acceptable adjuvants or immunomodulators, as desired, to mediate and/or enhance the immune response in the bird. Adjuvants such as muramyldipeptide (MDP), lipopolysaccharides, lipid A, polysaccharides, toxins, alginates, aluminum hydroxide, aluminum phosphate, bentonite, latex, agarose, cellulose, acrylic particles, polyadenylic-polyuridylic acid (poly A:poly U) saponin, vitamin A and/or E, concavilin A, avridine, etc. Examples of suitable immunomodulators are described, for example, in Hudson and Hay, *Practical Immunology*, pages 423–441, Blackwell Scientific Publications, London (1989); and Male et al., *Advanced Immunology*, pages 11.1–11.16, J. B. Lippincott Co., Philadelphia, Pa. (1991).

C. Additives.

The implant may be formulated with one or more additives to maintain isotonicity, physiological pH and stability, for example, a buffer such as physiological saline (0.85%), phosphate-buffered saline (PBS), citrate buffers, Tris (hydroxymethyl aminomethane (TRIS), Tris-buffered saline and the like, and/or a preservative such as thimersol, formalin, glutaraldehyde, or an antibiotic, for example, neomycin or streptomycin, etc.

It is also envisioned that the immunogen may be combined with a biocompatible, and optionally synergistic, immunomodulator that cooperatively stimulates antibody production, as for example, recombinant cytokines such as TGF-beta, interferons, activating factors, chemoattractants, interleukins such as IL-1, IL-2, IL-4, IL-5, IL-6, complex plant carbohydrates such as Acemann (available from Fort Dodge Animal Health), and microbial polysaccharides isolated from Xathomonas spp. and Pseudomonas spp. and other similar substances.

III. Dosage and Administration of Immunogens

The implant may be used to immunize against disease caused by one or more pathogenic organisms such as a virus, bacteria, fungi, mold, protozoa, etc. The particular formulation chosen will depend upon the agent against which immunization is sought, and the desired release rate. The choice is within the knowledge of one skilled in the art.

The implant is formulated with an effective amount of the immunogen to provide a primary immune response. The "effective amount" of the immunogen included in the implant matrix is based on the desired release profile, the concentration of immunogen necessary for stimulating a desired primary immune response, the immuno competency, the age and weight of the bird after hatching at the time of release of the immunogen, etc.

There is generally no maximum amount of the immunogen that is incorporated into the implant matrix, except for physical limitations that allow the immunogen to be held within the matrix and released in a predetermined manner. Generally, in some embodiments, the implant can be formulated as a single unit or multiples thereof to contain about 25–5000 $\mu$g of the immunogen of the implant matrix, preferably about 100–2000 $\mu$g, preferably about 250–1000 $\mu$g. The amount of immunogen released from the implant is preferably sufficient to induce a primary immune response in the bird.

The implant can be formulated to provide a sustained release, delayed release, or a combination thereof, of the immunogen, after or before hatching. In one embodiment, a sustained release implant can provide for immunogen release from the implant beginning at about 24 to 72 hours post administration. For example, as described in U.S. Pat. No. 5,569,468 to Modi et al.; U.S. Pat. No. 4,452,775 to Kent et al.; U.S. Pat. No. 4,863,735 to Kohn et al.; and U.S. Pat. No. 4,756,907 to Beck et al. An implant that is implanted in ovo into turkeys at about 26 days of incubation can be formulated to begin sustained release of an immunogen at, for example, about 1–21 days after hatching and continue release until about 90 days post hatching. See e.g., U.S. Pat. Nos. 4,897,268; 5,641,745; and 4,709,765.

Preferably, a sustained release implant is formulated to provide a sustained release of a linear dosage amount of the immunogen into the bird over the desired time period, for example, over a period of about 1–90 days, typically about 1–60 days, preferably about 1–35 days post hatching.

For example, a cholesterol-based 60-day release implant pellet (Innovative Research, Saratoga, Fla.) containing about 25–5000 $\mu$g of protein antigen per mg implant matrix, for example, *E. coli* siderophore protein antigen, maintaining a linear release, will release on a daily basis, about 0.4–83 $\mu$g/day of protein immunogen. A similar cholesterol-based 21-day implant containing about 5000 $\mu$g protein antigen will release about 238 $\mu$g/day, and a 90-day implant will release about 56 $\mu$g/day. Thus, the implant can be formulated to include an amount of an immunogen which provides the desired amount of antigen release over a predetermined time period.

As discussed above, a delayed release implant provides a burst release of the immunogen at a predetermined time post hatching. The time at which maternal antibody concentrations decrease can vary between birds. However, generally, maternal antibody concentrations decrease at about 7 to 28 days post hatching. Hence, to provide the immunogen at a time when maternal antibodies are sufficiently reduced to provide an immunizing effect, typically the immunogen of a delayed release implant is released at about 7 to 21, preferably about 14 to 28 days post hatching.

The in vivo release rate and extent of release of the immunogen from the solid implant matrix may be effectively controlled and optimized, for example, by varying the matrix formulation according to the desired duration or time interval for maintaining the solid matrix within the implant site, and by varying the type and amount of adjuvants and additives, such as plasticizing agents, and by the size, shape, porosity, solubility and biodegradability of the matrix, among other factors, according to practices known and used in the art. The timed release of the immunogen can be achieved and varied changing the exterior coating of the implant which could be based on the dissolvability, porosity or erodability of the implant. The release of the immunogen from, the matrix may also be varied according to the form and solubility of the immunogen in tissue fluids, the distribution of the immunogen within the matrix and the properties of the matrix including porosity, electrical charge, dissolvability, diffusion, etc.

After a primary immune response has been stimulated, a booster immunization can be optionally administered to enhance or stimulate a secondary immune response. A booster can be in the form of a second implant containing the immunogen, an injectable liquid vaccine, a modified live vaccine, a natural exposure to the immunogen/pathogen, or other suitable means. For example, a booster effect in a bird administered a primary immunization with conserved proteins as SRPs and porins may come from a natural field exposure with a bacteria that expresses these proteins that will cause a rise in anti-SRP-porin antibody titers.

Alternatively, a booster injection can be provided in a single implant or multiple implants. For example, a sustained release and delayed release matrix can be combined in a single implant or multiples thereof. According to this embodiment, sustained release of the immunogen can occur post hatching to prime the immune system and subsequently a delayed burst of the immunogen stimulate a secondary response.

An animal may also be boostered to stimulate a secondary response by natural exposure or a booster may be given by any suitable route such as intramuscular, subcutaneous, intranasally, intraocular, orally, cloacal, etc. administration of a killed antigen or modified live vaccine.

The amount of immunogen released from an implant to provide a primary immune response is preferably sufficient to induce a secondary immune response in the bird upon delivery of the booster immunogen and/or upon challenge by a pathogenic organism. Preferably, the active antibody titer after a booster or post-challenge, is detectable up to a dilution factor of about 10–1000, typically about 5–500.

In ovo administration of the implant is ultimately done with the guidance of a veterinarian or other animal-care or animal processing professional. The implant is administered into an egg, through the shell, by injection into the side or, preferably, the top of the egg using known methods. As used herein, the "top" of the egg is the large or blunt end where the air cell develops during incubation. The implant can alternatively be administered in the yolk sac which is typically accessed best by injection into the side of the egg. The egg can also be injected into the albumen at the small end or bottom of the egg.

Preferably, the implant is injected into the blunt end of the egg using a hypodermic syringe with a needle of about 14–21 gauge, that is inserted about 10–40 mm into the egg, or according to standard techniques known in the art such that there is no or little entry of air through the injection hole into the egg. Preferably, the injection hole is sealed with a non-permeable material such as a silicone sealant, or other like material, to prevent entry of microorganisms.

For turkeys, the implant is preferably administered in the eggs on about the 23–28 day of incubation (embryonic development), preferably on about the 24–27 day, preferably on about the 25–27 day of incubation. For chickens, the implant is administered into the eggs on about 17–21 days of incubation, preferably on about 17–19 days, preferably on about 17–18 days of incubation. The implant can be administered prior to or after transfer. In turkeys, transfer typically occurs at about day 25 and in chickens transfer typically occurs at about day 18. Incubation periods for some birds are provided in Table I below.

TABLE 1

AVERAGE INCUBATION PERIODS FOR POULTRY

| Species | Incubation period (days) |
|---|---|
| Chicken: | |
| Light-type | 21 |
| Broiler-type | 21 |
| Turkey | 28 |
| Goose | 28–32 |
| Duck (Pekin) | 28 |
| Pheasant | 24 |
| Quail (bobwihte) | 23–24 |
| Pigeon | 18 |
| Guinea fowl | 27 |

A high speed, automated egg injection apparatus that will process a plurality of eggs and provide for precise injection of the implant into the desired location in the eggs can be useful. Such apparatuses are known and used in the art. The apparatus can include an egg aligning mechanism to position and align the eggs in relation to the injection needle as desired and an automatic injection needle to inject the implant through the shell and into the interior of the egg. A preferred apparatus that is commercially available is The INOVOJECT® system from EMBREX, INC., Morrisville, N.C.

The following Examples are provided to further describe preparation and administration of one presently preferred implant formulation according to the invention. The Examples, however, are not in any way intended to limit the products and processes which fall within the spirit and scope of the invention.

IV. EXAMPLES

Example 1

Preparation of Combined Sustained/Delayed Release Microsphere Implants 3 g of medium viscosity alginic acid (Keltone HV, Monsanto Chemical Co.), was dissolved into 100 ml of 0.04 M sodium phosphate pH 5.7. The resulting suspension was blended at 3000 rpm for 10 minutes using a Dyna-mix stirrer with a 18 inch stainless steel impeller (Fisher Scientific, Pittsburgh, Pa.) until a homogenous solution was formed. Xanthan gum (1.5%) (Xanthural 11K, Monsanto Chemical Co.) was prepared in 0.04 M sodium phosphate and added to the alginic acid to give a final xanthan gum concentration of 0.023%. The xanthan gum and alginic acid solution was then mixed thoroughly and sterilized by autoclaving for 15 min at 121° C. The final viscosity of the mixture at 25° C. was approximately 3,500 cps. The solution was stored at 25° C. until it was used.

Spherical cellulose, dextran or agarose beads having a particle diameter of 50–150 $\mu$m and functionalized with diethylaminoethyl (DEAE) to give a negative charge to the beads was obtained commercially (Millipore Corp., Danvers, Mass.). The negatively charged beads were activated by washing the slurry in 0.02 M sodium phosphate (pH 5.7) containing 0.5 M sodium chloride, followed by several washes with 0.02 M sodium phosphate (pH 5.7) without NaCl. The activated bead slurry was combined with the SRP antigen at 1–20 mg/ml. The bead-antigen slurry was mixed at 200 rpm/min at 4° C. for 24 hours at which point the slurry was allowed to settle. The antigen bound beads were then washed 2 times in 0.02 M sodium phosphate buffer by settling to remove any non-bound antigen. The supernatant was removed without disrupting the antigen-bead slurry. The concentration of antigen bound to 100 $\mu$l of bead slurry was 941 $\mu$g, as determined using a Pierce BCA Protein Assay, Rockford, Ill. The alginic acid solution was added to the bead slurry to give a final bead/alginic acid ratio of 1.5:7.5 vol./vol. or 20%. The suspension was mixed well to disperse the beads as a homogenous suspension. To this suspension, SRP-Porin antigen was added to give a concentration of free antigen of 250 $\mu$g/ml. This solution, containing bound and non-bound SRP antigens, was formed into microspheres.

The formation of microspheres and/or macrospheres can be accomplished by any type of droplet generating devices. Examples of suitable droplet generating devices include the air knife, electrostatic droplet generator and a spinning disc droplet generator as described in U.S. Pat. No. 5,578,314, the entire disclosure of which is incorporated herein by reference.

The alginic acid droplets generated by any of the above-mentioned devices are collected in calcium or other divalet cation solution causing the alginate to gel, forming a solid spherical shape, as illustrated in FIG. 1. FIG. 1 illustrates an alginate microsphere 1 containing antigen bound cellulose beads 2 dispensed throughout the alginate microsphere 1, as well as non-bound antigen 3 within the matrix 4. The microspheres now containing bound and non-bound antigen were formulated into a syringeable vaccine by density stabilizing the solution with xanthan gum.

Example 2
Evaluation of Antigen Release from Microsphere Implants in Poults

Microspheres were prepared as described in Example 1 and including the SRP-Porin antigens of *Pasteurella multocida* P-1059. The SRP Porin antigen suspension was adjusted to three different concentration, 250 µg, 500 µg and 1000 µg per bird dose. A placebo was prepared containing all ingredients except the SRP-Porin antigen and was used as the control dose.

200 forty-day-old turkey poults (hybrid hens) were obtained from Willmar Poultry Company's Commercial hatchery, (Willmar, Minn.) and equally divided into four groups, designated as I–IV. All birds received a 0.5 cc subcutaneous injection of the appropriate vaccine implant in the lower neck region (group I-controls, group II-250 µg; group III-500 µg and group IV-1000 µg). Birds were colored to maintain identity of treatment groups and randomly distributed between two isolation rooms.

Figure 2:
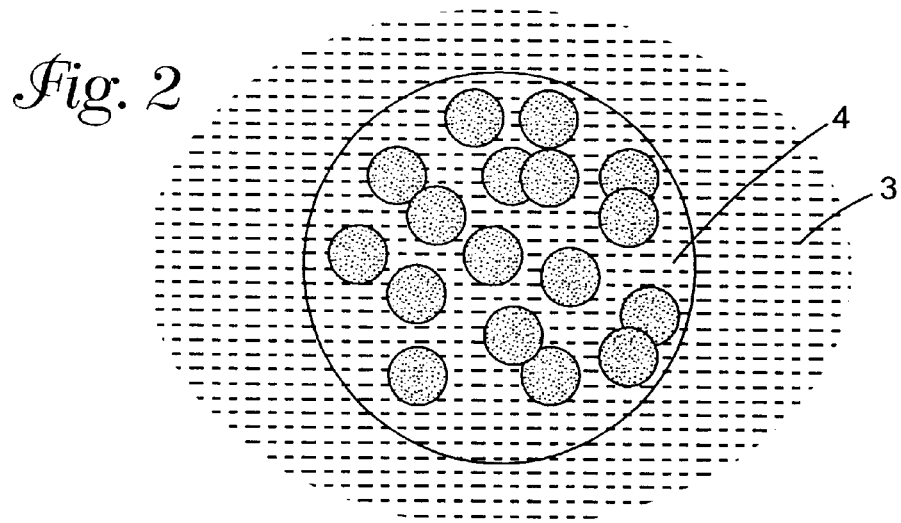
FIG. 2 is a diagrammatic illustration of the implant of FIG. 1 after being implanted in the tissues of a bird for approximately 14–21 days.

At 7 day intervals through eight weeks of age, four birds/group were killed by euthanasia and the injection sites were examined for any adverse tissue reaction. Birds necropsied at 7 days of age showed a slight inflammatory response. The microspheres did not migrate from the injection site, but rather formed a depot at the site of injection. Referring to the FIG. 2, microscopic examination of the implanted material revealed that the microspheres 1 were still completely intact, substantially as illustrated in FIG. 1. However, there was a significant influx of mononuclear cells consisting of small lymphocytes and macrophages within the interstitial fluid of the implanted material. This was more pronounced in groups II–IV in contrast to the placebo which had a minimal influx of mononuclear cells. A close examination of the microspheres revealed a complete to partial monolayer of cells attached to their outside surface, presumably macrophages. This was more pronounced in the 1000 µg treatment group then in any of the other groups including the placebo. This was consistent for the 14 and 21-day sampling period. As depicted in FIG. 2, during this time the non-bound antigen 3 is released into interstitial tissue.

Figure 3:
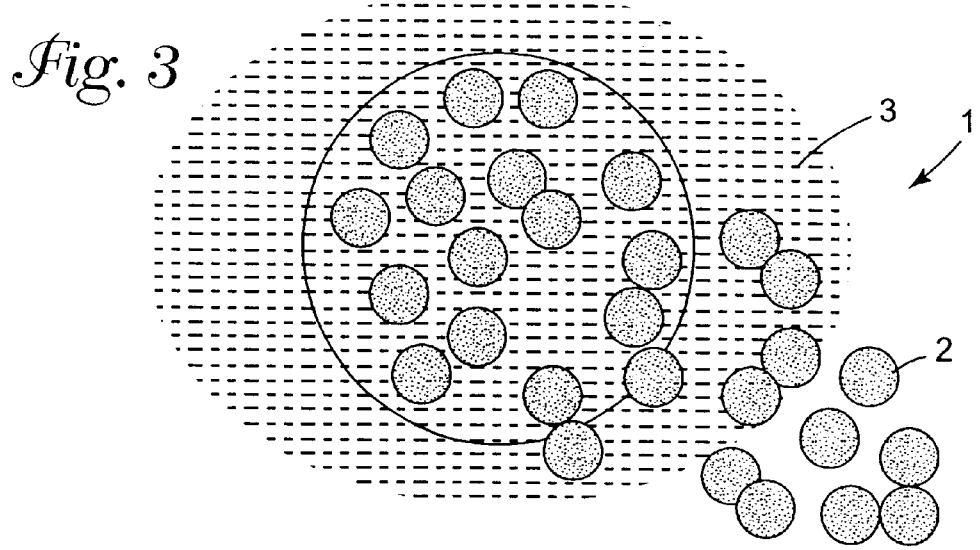
FIG. 3 is a diagrammatic illustration of the implant of FIG. 1 after being implanted in the tissues of a bird for more than 21 days.

As illustrated in FIG. 3, beginning at about 21 days, the microspheres 1 in the 500 µg and 1000 µg groups were beginning to deteriorate. Many of the antigen bound cellulose beads were outside the microspheres within the interstitial fluid of the implanted material. The antigen bound cellulose beads 2 were similar to those in the intact microsphere at 7 days in that a monolayer of cells surrounded the bead 2. The microspheres in the placebo and 250 µg groups were still intact. At twenty eight days, the microspheres in the 500 and 1000 µg dose groups had completely lost their spherical integrity and the implanted material had a pasty, highly viscous consistency. Upon microscopic examination, the cellulose beads were free within the implanted material surrounded by mononuclear cells. At this same time frame the microspheres in the control and 250 µg group began to deteriorate but to a lesser degree as compared to the 500 and 1000 µg groups at this same time period. At thirty-five days the microspheres in the placebo and 250 µg group had lost all spherical integrity while there was a reduction in the size of the implanted material in the 500 and 1000 µg group. Microscopic examination, revealed cellulose beads outside the implanted material were surrounded by mononuclear cells as deterioration progressed.

Deterioration of the implanted material progressed in all groups and by eight weeks 95% of the birds examined had no implanted material remaining. However, a number of birds in the 500 and 1000 µg dose group had a small residual plaque remaining. None of the birds in any of the groups examined revealed adverse tissue reaction to the implanted material.

Example 3
Vaccination of Poultry with Siderophore Receptor Proteins-Porins Incorporated in Alginic Acid Microspheres Microspheres were prepared as described in Example 1 containing the SRP-Porin antigens of *Escherichia coli*. A placebo was prepared containing all ingredients of the microspheres except the SRP-porin antigen and was used for the non-vaccinated control group.

Twelve hundred-day-old turkey poults (hybrid hens) were obtained from Willmar Poultry Company's commercial hatchery (Willmar, Minn.) and equally divided into three Groups designated as A, B and C. All birds in Groups A and C received a 0.5 cc subcutaneous injection of micro spheres. Group A received the placebo and remained as non-vaccinated, implanted controls. Group C received 0.5 cc of the SRP-porin containing microspheres at a bird dose of 941 µg. Group B received no microspheres or other vaccine and remained as non-vaccinated, non-implanted birds.

Each Group (A, B, C) of birds were colored at the hatchery to maintain identity and subsequently divided into two separate sub-groups (i.e, $A_1$, $A_2$, $B_1$, $B_2$, $C_1$, $C_2$). Test groups 1 and 2 were formed with one subgroup of 200 birds from the Groups (i.e., Test group 1=$A_1$+$B_1$+$C_1$ and Test group 2=$A_2$+$B_2$+$C_2$). Each Test group (600 birds) was placed in a pen on separate brooding farms and reared under commercial conditions.

At four weeks of age, all birds in Test groups 1 and 2 were maintained in separate pens on different grow out farms. The square footage of each pen was adjusted to match commercial rearing conditions.

At three weeks of age, all birds in Group B from Test groups 1 and 2 were vaccinated with 300 µg SRP-porin antigen emulsified in Freunds incomplete adjuvant.

Figure 5:
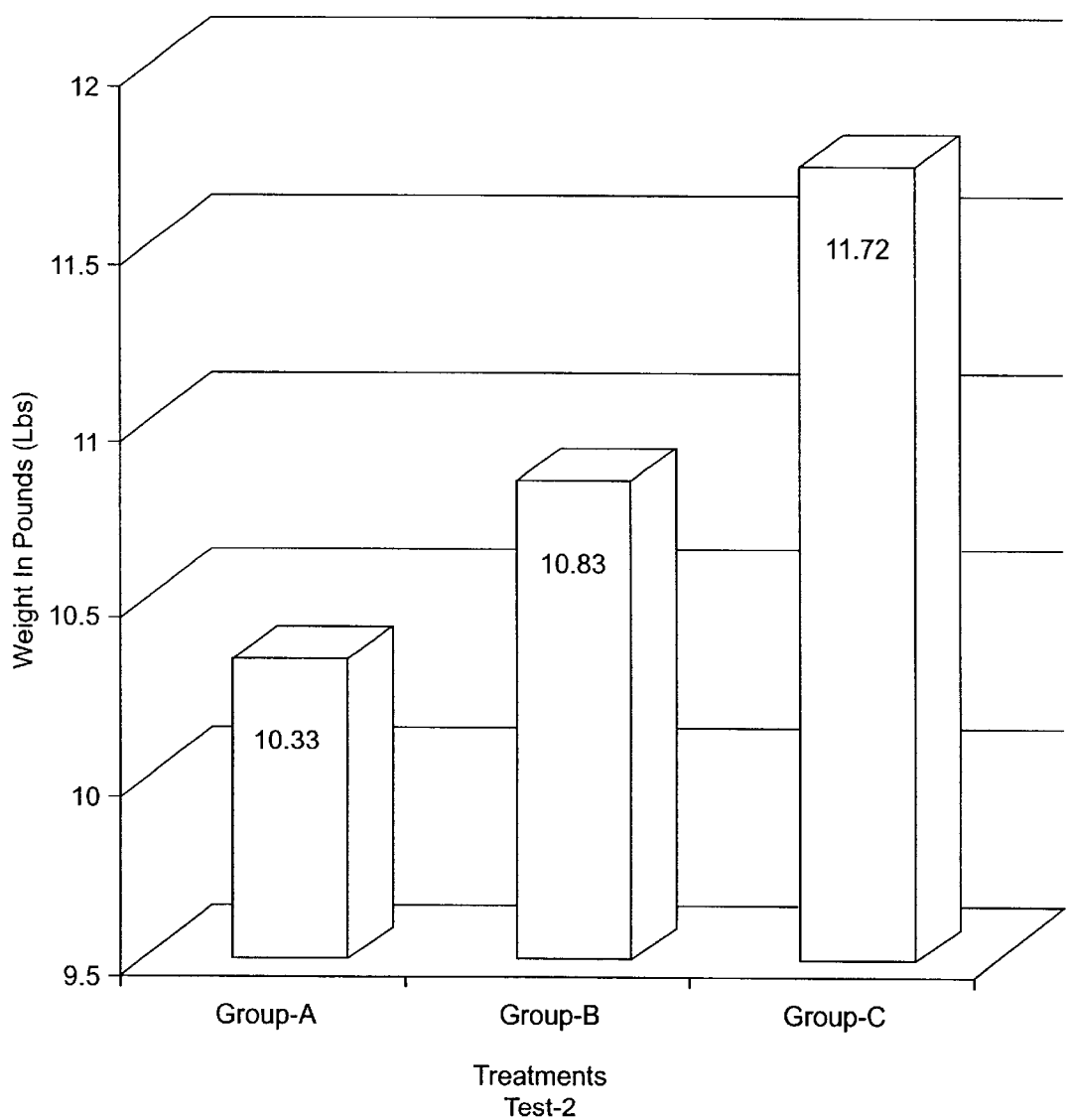
FIG. 5 is a graph showing weight comparison at 11 weeks of age between non-vaccinated microsphere controls (Group A), SRP administered at 3 weeks of age (Group B) and hatchery administered SRP in microspheres (Group C) in commercial turkeys (Test group 2).

All birds in Test group 1 were individually weighed at 1, 4, 6, 8 and 11 weeks post vaccination. In contrast, all birds in Test group 2 were weighed at 11 weeks for a comparison of the final weight between Test groups (FIG. 5). Table 2 shows the comparison of weights between Groups A, B and C of Test group 1.

TABLE 2

Comparison of Average Weight (lbs.)
Between Groups A, B and C of Test Group 1

| | Treatment | | |
|---|---|---|---|
| Weeks post-treatment | Group A 1-day Microsphere Placebo | Group B 3-wk SRP-vaccination | Group C 1-day SRP Microsphere Vaccination |
| Week 1 | 0.273 | 0.280 | 0.289 |
| Week 4 | 1.51 | 1.50 | 1.50 |
| Week 6 | 3.32 | 3.24 | 3.36 |
| Week 8 | 6.19 | 6.01 | 6.29 |

TABLE 2-continued

Comparison of Average Weight (lbs.)
Between Groups A, B and C of Test Group 1

| | Treatment | | |
|---|---|---|---|
| Weeks post-treatment | Group A 1-day Microsphere Placebo | Group B 3-wk SRP-vaccination | Group C 1-day SRP Microsphere Vaccination |
| Week 11 | 10.58 | 10.75 | 11.60 |

Referring to Table 2, there was a significant difference in weight between Groups, with Group C being the heaviest at 6, 8 and 11 weeks post vaccination as compared to birds in Groups A and B. At 11 weeks of age, birds in Groups B and C were both heavier than birds in Group A (control). However, the birds in Group C were 1.02 pounds heavier than birds in Group A and 0.67 pounds heavier than birds in Group B, raised under identical conditions. It is interesting to note there was a slight suppression in weight in Group B at 6 and 8 weeks of age, in contrast to Groups A and C at the same time frame. This is often characteristic of a water-in-oil emulsion which can cause an adverse tissue reaction at the site of injection which can cause stress to the bird leading to a loss in performance. Nevertheless, birds in Group C which received three times the concentration of SRP at one day of age showed no loss in weight as compared to Group B.

Figure 4:
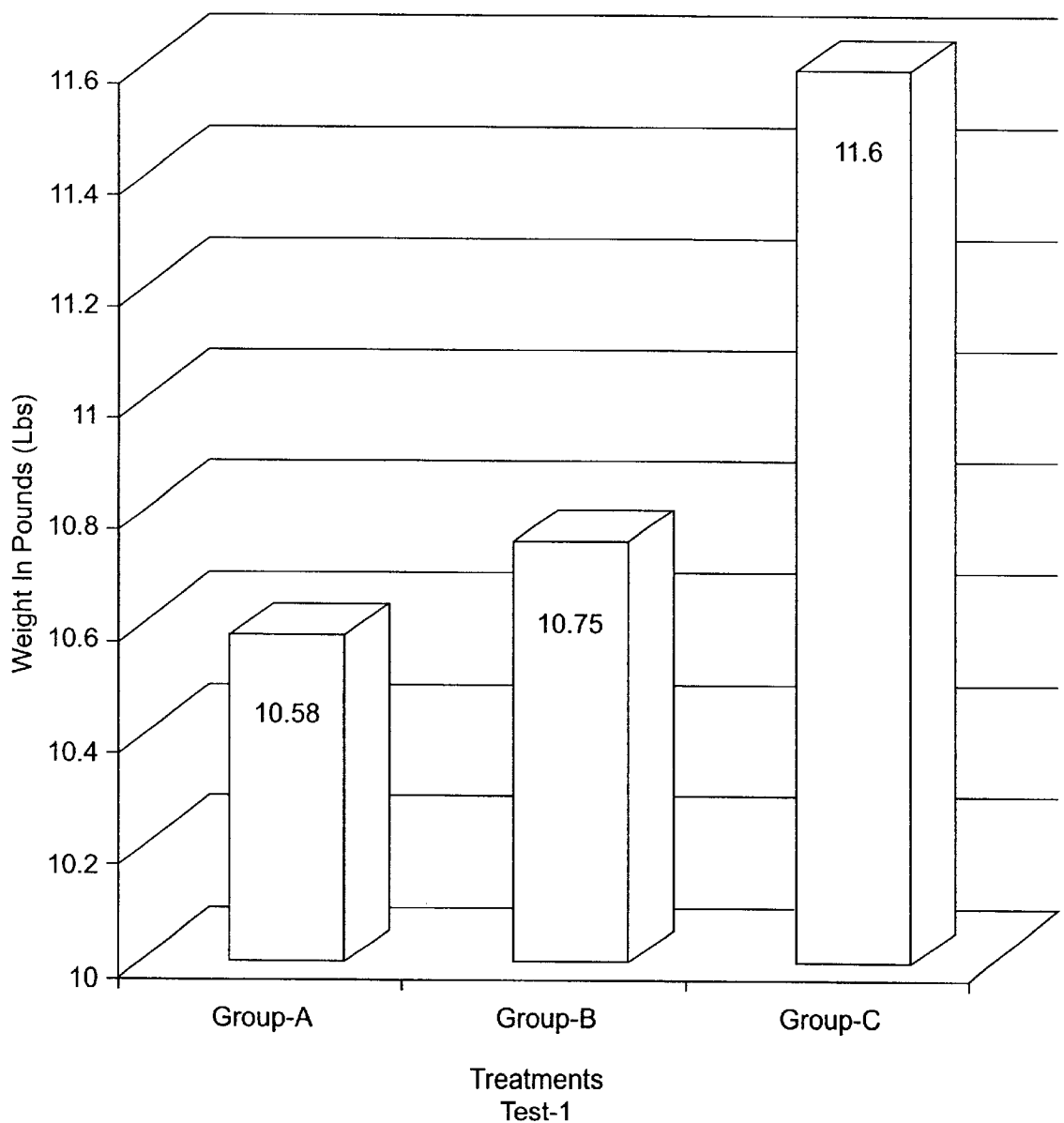
FIG. 4 is a graph showing weight comparison of birds at 11 weeks of age between non-vaccinated micro sphere controls (Group A), SRP administered at 3 weeks of age (Group B) and hatchery administered SRP in microspheres (Group C) in commercial turkeys (Test group 1)

FIGS. 4 and 5 show the difference in weight between Groups A, B and C in Test groups 1 and 2 at eleven weeks of age. As can be seen, Groups B and C were significantly heavier as compared to Group A (controls) with Group C in both Test groups 1 and 2 being heavier than either of the other two Groups (A and B).

Example 4
Clinical Challenge and Performance of in ovo Immunized Birds

One hundred embryonated eggs, at 20 days of embryogenesis, were removed from one of Willmar Poultry Co.'s commercial incubators. The blunt or air cell end of each egg was first disinfected with 70% isopropyl alcohol. Each egg was punctured by drilling a small hole in the center using a 1/16 inch carbide tipped bit attached to a battery-operated dremel.

Using a 1¾ inch stainless steel 21 gauge needle, each embryo was injected with a volume of 0.25 cc of microspheres containing 500 µg SRP-Porin antigen as described in Example 1. The needle was injected parallel to the longitudinal axis of the egg at a depth of approximately 1½ inches. All eggs were inoculated within 40 minutes from the time they were removed from the incubator. All of the inoculation holes were sealed with super glue and returned to the incubator. At 24 days of age these eggs were removed from the incubator and placed into a designated hatching tray and placed in a commercial hatcher along with the remaining sister eggs.

Eighty six percent of the in ovo-inoculated eggs hatched in contrast to the sister eggs at 89%. None of the in ovo vaccinated poults appeared to have any adverse effects due to the vaccination. Fifteen of these birds were euthanized by (carbon dioxide) $CO_2$ and necropsied to examine the site of injection. Injection sites having implant material was identified in eleven birds, which varied in location from the upper to lower neck to the upper back. No injection sites were found in the remaining birds and were presumed to be misses. If these birds were representative of the 86 that hatched it would mean that 73% were vaccinated.

V. Other Applications

The timed release implants of the present invention can also be used for timed delivery of an agent into the tissues of livestock such as fish. The implants of the hinvention can be particularly advantageous for immunization of fish at a predetermined time after hatching.

All patents and publications referred to in the present disclosure are incorporated herein by reference.

In the foregoing detailed description, it will be evident that modifications and variations can be made to the products and methods of the invention without departing from the spirit or scope of the invention. Therefore, it is intended that all modifications and verifications not departing from the spirit of the invention come within the scope of the claims hereinafter appended.

What is claimed is:

1. A method for inducing immunity in a bird against a selected immunogen comprising:
    injecting a biocompatible implant in ovo, wherein the biocompatible implant comprises the selected immunogen and a bicompatible matrix material, wherein the implant provides for sustained and delayed release of e immunogen until a time when maternal antibodies of the bird to the immunogen are sufficiently reduced so that the bird is capable of mounting an immune response to the immunogen, wherein the implant is comprised of beads suspended in an alginate microsphere.

2. The method according to claim 1, wherein immunogen is bound to the beads.

3. The method according to claim 1, wherein the immunogen is present unbound in the alginate microsphere and immunogen is bound to the beads.

4. The method according to claim 1, wherein the implant is injected during the fourth quart of incubation of an egg.

5. The method according to claim 1, wherein the implant is injected at about 15–28 days of incubation of an egg.

6. The method according to claim 1, wherein the bird is selected from the group consisting of turkey, chicken, duck, goose, ostrich and pheasant.

7. The method according to claim 1, wherein the bird is a turkey and the implant is injected at about 25–27 days of incubation of an egg.

8. The method according to claim 1, wherein the implant provides for sustained release of the immunogen for about 1–90 days post-hatching.

9. The method according to claim 1, wherein the implant provides for sustained release of the immunogen for about 1–60 days post-hatching.

10. The method according to claim 1, wherein the implant provides for sustained release of the immunogen for about 1–35 days post-hatching.

11. The method according to claim 1, wherein the implant is injected at about 25–27 days of incubation of an egg and wherein the implant provides for sustained release of the immunogen for about 1–90 days post-hatching of the egg.

12. The method according to claim 1, wherein the bird is a chicken and the implant is injected at about day 17 to 19 of incubation of an egg.

13. The method according to claim 1, farther comprising administering a second dose of e immunogen at 3–12 weeks post hatching to stimulate a secondary immune response.

14. The method according to claim 1, wherein the implant provides for delayed release of the immunogen at about 71 to 28 days post hatching.

\* \* \* \* \*

UNITED STATES PATENT AND TRADEMARK OFFICE
CERTIFICATE OF CORRECTION

PATENT NO. : 6,682,754 B2
DATED : January 27, 2004
INVENTOR(S) : Emery et al.

It is certified that error appears in the above-identified patent and that said Letters Patent is hereby corrected as shown below:

<u>Title page,</u>
Item [56], References Cited, "Griffiths, E. et al.," reference, delete "*coli*express" and insert -- *coli* express --.

<u>Column 18,</u>
Lines 22 and 61, delete "e" and insert -- the --
Line 35, delete "quart" and insert -- quarter --
Line 64, delete "71" and insert -- 7 --

Signed and Sealed this

Twenty-seventh Day of April, 2004

JON W. DUDAS
*Acting Director of the United States Patent and Trademark Office*

UNITED STATES PATENT AND TRADEMARK OFFICE
CERTIFICATE OF CORRECTION

PATENT NO.       : 6,682,754 B2
APPLICATION NO.  : 09/449271
DATED            : January 27, 2004
INVENTOR(S)      : Emery et al.

It is certified that error appears in the above-identified patent and that said Letters Patent is hereby corrected as shown below:

Title Page
Item [54] Title, delete "OVO DELIVERY OF AN IMMUNOGEN CONTAINING IMPLANT" and insert --IN OVO DELIVERY OF AN IMMUNOGEN CONTAINING IMPLANT--

Column 1
Line 1, delete "OVO DELIVERY OF AN IMMUNOGEN CONTAINING IMPLANT" and insert --IN OVO DELIVERY OF AN IMMUNOGEN CONTAINING IMPLANT--

Signed and Sealed this

Thirtieth Day of January, 2007

JON W. DUDAS
*Director of the United States Patent and Trademark Office*